United States Patent [19]
Bonner et al.

[11] Patent Number: 5,510,266
[45] Date of Patent: Apr. 23, 1996

[54] METHOD AND APPARATUS OF HANDLING MULTIPLE SENSORS IN A GLUCOSE MONITORING INSTRUMENT SYSTEM

[75] Inventors: Lydia M. Bonner, Leesburg; Joseph P. Desimone, Mishawaka; Russell J. Micinski, South Bend, all of Ind.

[73] Assignee: Bayer Corporation, Elkhart, Ind.

[21] Appl. No.: 435,201

[22] Filed: May 5, 1995

[51] Int. Cl.$^6$ ................................................ G01N 37/00
[52] U.S. Cl. ...................... 436/43; 436/46; 422/58; 422/61; 422/63; 422/99; 422/104; 221/87; 221/88; 221/268
[58] Field of Search .................. 436/43, 46; 422/55, 422/58, 61, 63, 68.1, 99, 102, 104; 221/87, 88, 268

[56] References Cited

U.S. PATENT DOCUMENTS

| | | | |
|---|---|---|---|
| 4,576,591 | 3/1986 | Kaye et al. | 604/62 |
| 4,667,845 | 5/1987 | Frazier et al. | 221/5 |
| 4,785,969 | 11/1988 | McLaughlin | 221/2 |
| 5,405,011 | 4/1995 | Haber et al. | 206/531 |

*Primary Examiner*—Jill Warden
*Assistant Examiner*—Long V. Le
*Attorney, Agent, or Firm*—Jerome L. Jeffers

[57] ABSTRACT

A sensor dispensing instrument includes a sensor magazine that contains a plurality of blood glucose sensors disposed in sensor slots. Each of the sensor slots is in fluid communication with a desiccant cavity in which desiccant material is disposed. The front and rear walls of the sensor magazine are sealed with burst foils so as to seal the sensor slots and the desiccant cavities. The sensor instrument has an outer housing with a laterally extending magazine opening adapted to receive the sensor magazine. A pivot rod is moved through the magazine and an indexing wheel into an operating position with a detent arm on the instrument housing engaging a detent groove on the magazine to position the magazine in a sensor feeding position. Once so positioned, a sensor push rod is pushed forward resulting in the push rod piercing the rear burst foil and engaging a sensor in one of the sensor slots to thereby push the sensor out through the front burst foil and into a testing position. Once a test is completed, the push rod is advanced forward further to thereby eject the used sensor from the sensor handling instrument. The push rod then is retracted to a standby position. As the push rod is being retracted, a pin associated with the push rod causes the indexing wheel to rotate so that the pivot rod is rotated until the detent arm engages another detent groove so that another sensor slot is in alignment with the push rod.

18 Claims, 4 Drawing Sheets

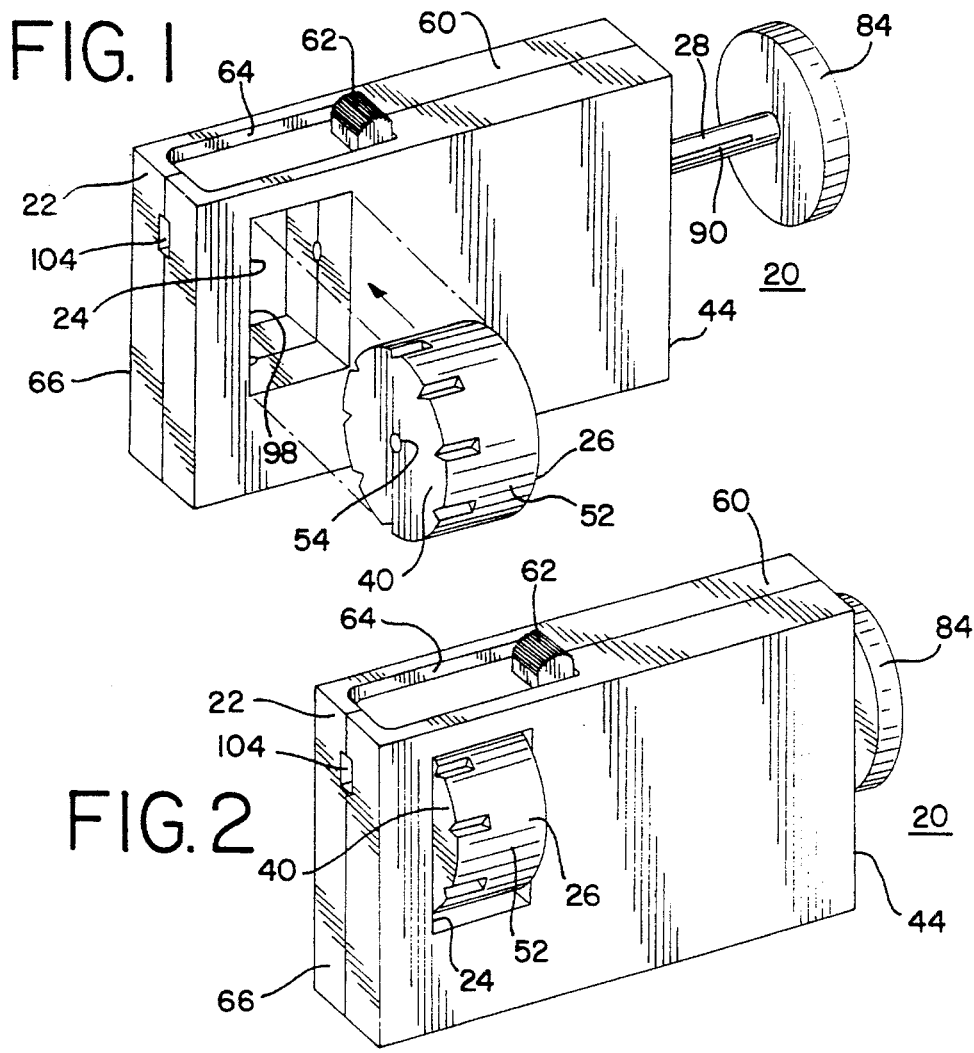
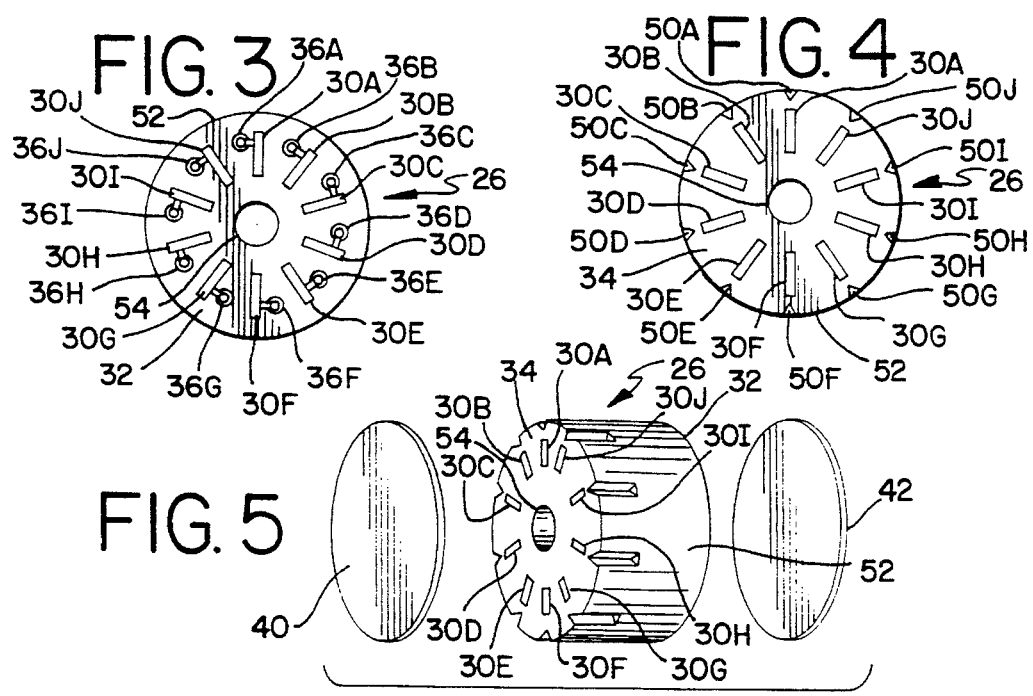

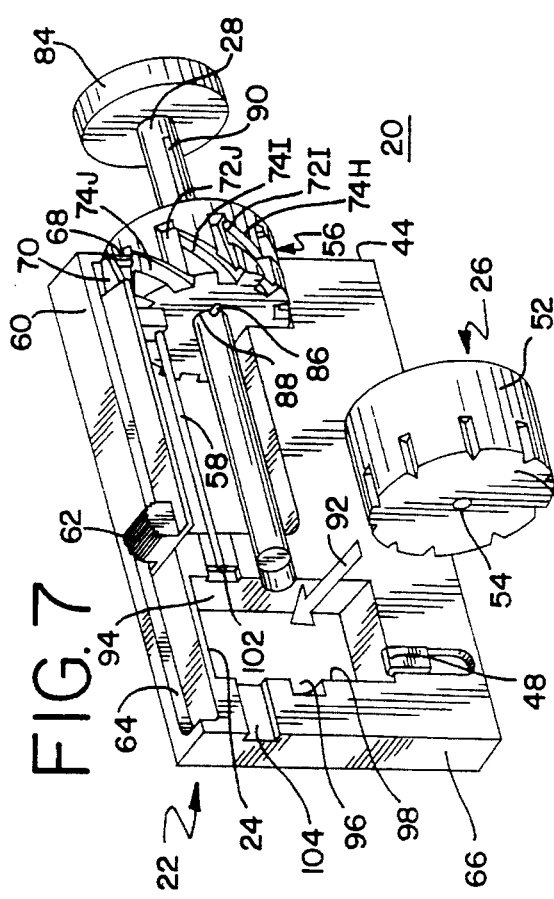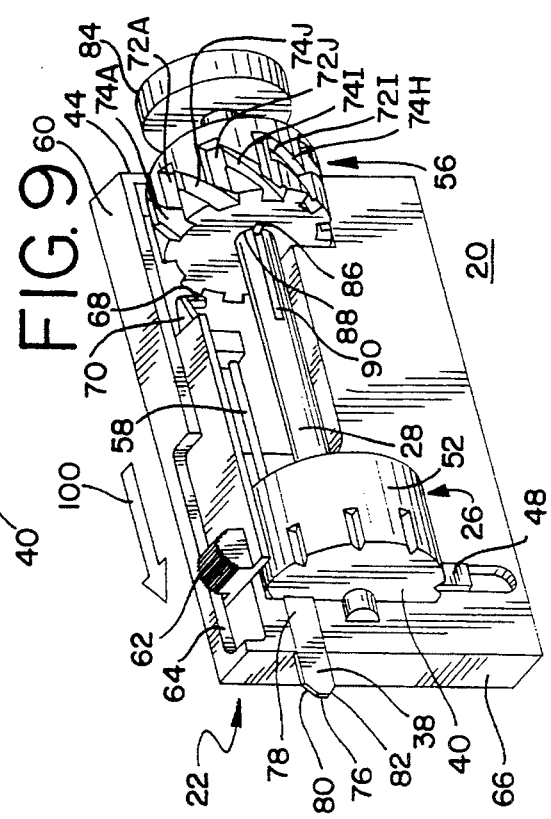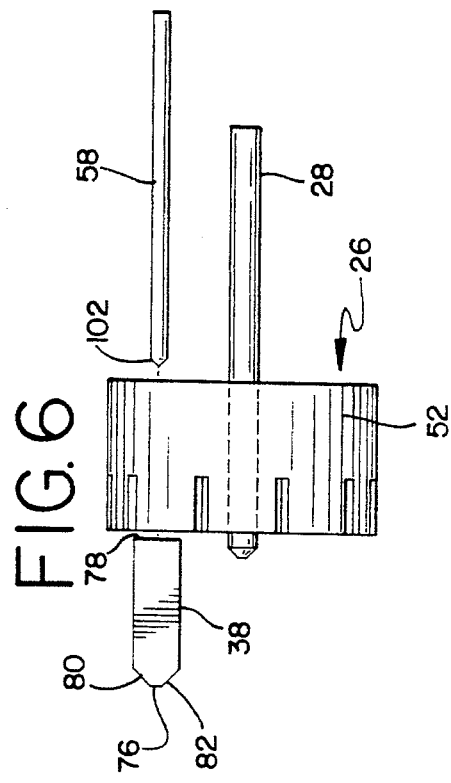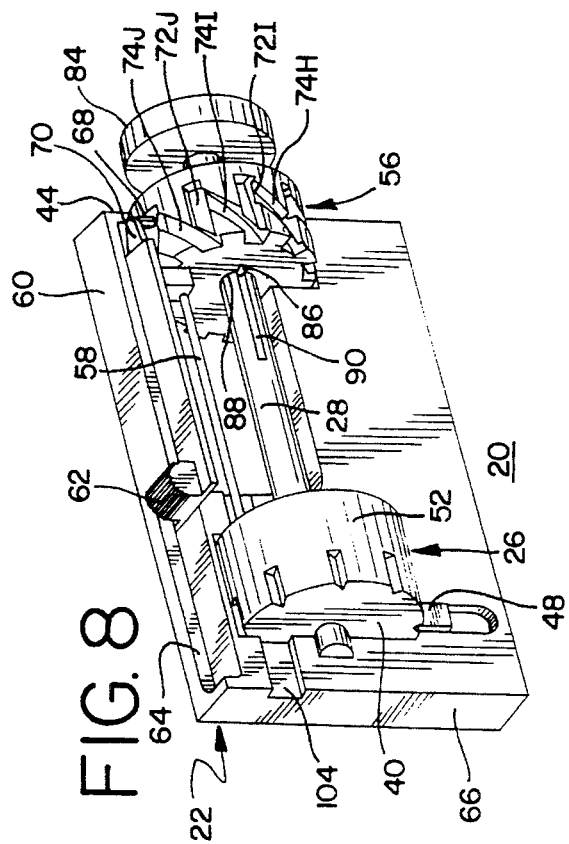

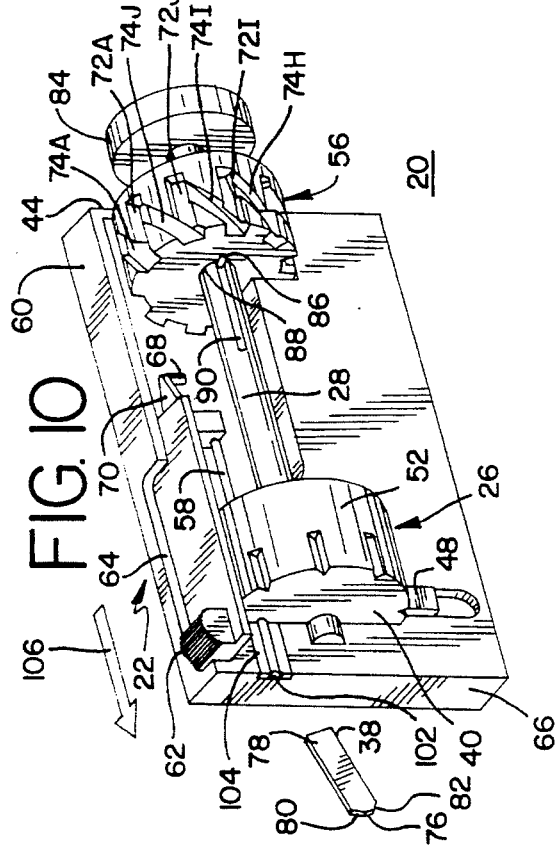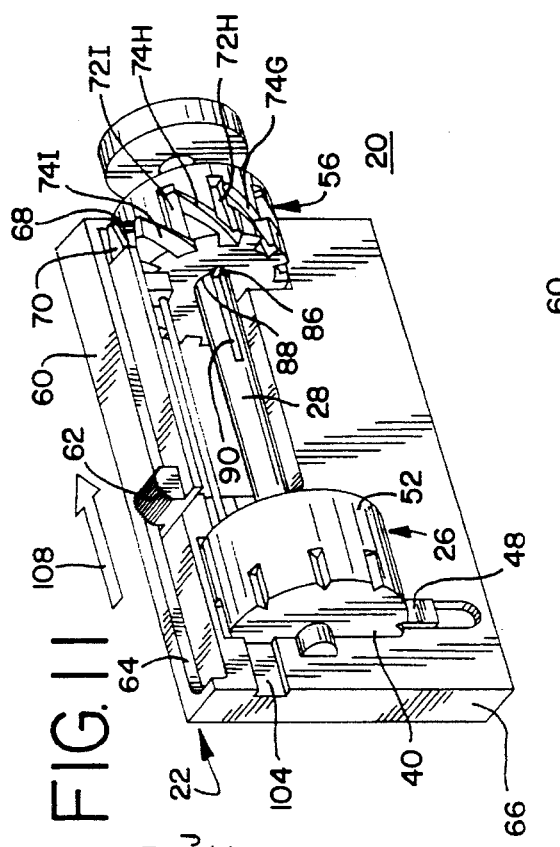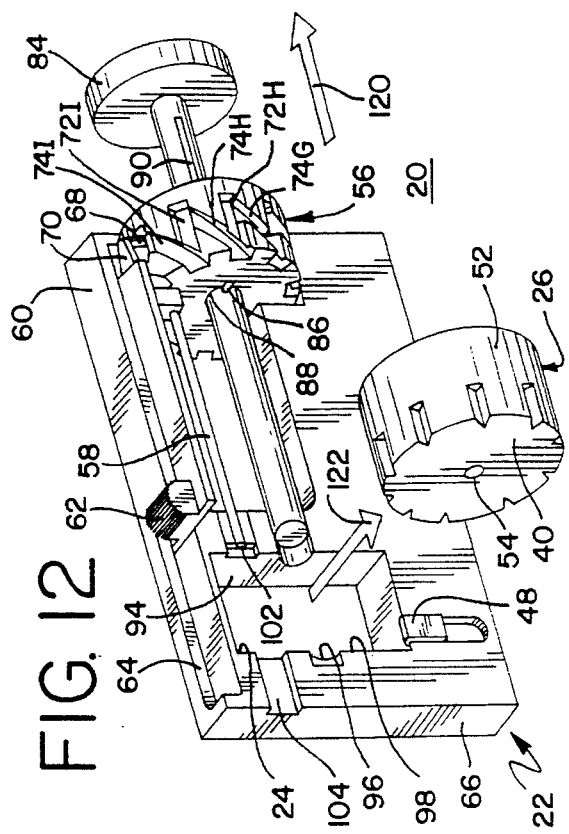

5,510,266

METHOD AND APPARATUS OF HANDLING MULTIPLE SENSORS IN A GLUCOSE MONITORING INSTRUMENT SYSTEM

BACKGROUND OF THE INVENTION

1. Field of the Invention

The present invention generally relates to a glucose monitoring system, and, more particularly, to a new and improved device for handling multiple sensors that are used in analyzing blood glucose.

2. Description of the Prior Art

People suffering from various forms of diabetes routinely need to test their blood to determine the level of blood glucose. The results of such tests can be used to determine what, if any, insulin or other medication needs to be administered. In one type of blood glucose testing system, sensors are used to test a sample of blood.

Such a sensor may have a generally flat, rectangular shape with a front or testing end and a rear or contact end. The sensor contains biosensing or reagent material that will react with blood glucose. The testing end is adapted to be placed into the fluid being tested and has a capillary channel that extends in the sensor from the testing end to the reagent material. The testing end of the sensor can be placed into blood that has accumulated on a person's finger after the finger has been pricked. The fluid is absorbed into the capillary channel of the sensor by capillary action so that the sensor acts as a wick for the fluid being tested. The fluid then chemically reacts with the reagent material in the sensor so that an electrical signal indicative of the blood glucose level in the blood being tested is supplied to contacts projecting from the rear or contact end of the sensor.

In order to couple the electrical signals produced at the sensor contacts to monitoring equipment, the sensors need to be inserted into sensor holders prior to the sensor end being placed into the fluid being tested. The holders have corresponding mating contacts that become coupled to the contacts on the sensor when the sensor is inserted into the holder. Consequently, the holders act as an interface between the sensor and monitoring equipment that accumulates and/ or analyzes the test results.

The sensors need to be maintain at an appropriate humidity level prior to being used so as to insure the integrity of the reagent materials in the sensor. Sensors can be packaged individually in tearaway packages so that they can be maintained at the proper humidity level. For instance, blister type packaging methods could be used. In this connection, the packages can include desiccant material to maintain the proper humidity or desiccate level in the package. In order for a person to use an individual sensor for testing blood glucose, the package must be opened by tearing the seal. Alternatively, some packages require the user to exert force against one side of the package resulting in the sensor bursting or rupturing the foil on the other side. As can be appreciated, the opening of these packages can be difficult. Moreover, once the package is opened, the user needs to be sure that the sensor is not damaged or contaminated as it is being placed into the sensor holder and used to test the blood sample.

SUMMARY OF THE INVENTION

Accordingly, an object of the present invention is to provide a new and improved device for handling multiple sensors used in testing blood glucose. Other objects of the present invention are to provide a new and improved blood glucose sensor handling device that enables a user to easily perform blood glucose testing; to provide a new and improved device for selectively placing one of a plurality of blood glucose sensors in position to be used for testing of a blood sample; to provide a new and improved blood glucose sensor handling device that contains a plurality a blood glucose sensors and that acts as an interface between the sensor and testing equipment when the sensor is being used; to provide a new and improved blood glucose sensor handling device that protects a plurality of sensors for use in testing of blood glucose from the environment in a desiccated condition until the sensor is to be used; to provide a new and improved blood glucose sensor handling device that is adapted to receive a sensor magazine containing a plurality of blood glucose sensors so that individual ones of the sensors can be selectively placed in a sensing position when a sensor actuator on the handling device is moved to a sensing position; and to provide a new and improved blood glucose sensor handling device that is adapted to receive a sensor magazine containing a plurality of blood glucose sensors and to automatically index the sensor magazine after one of the sensors has been used so that another one of the sensors can be readily placed into a sensing position.

In accordance with these and many other objects of the present invention, the present invention is embodied in a sensor dispensing instrument that is adapted to receive sensor magazines containing a plurality of blood glucose sensors. Each of the sensors has a generally flat, rectangular shape with a chamfered sensing end and an opposite contact end. The magazine may be in the form of a molded plastic right cylinder that contains a plurality of sensor slots that extend from a rear wall to a front wall. A series of detent grooves are disposed on the outer circumferential wall of the cylinder, each detent groove corresponding to one of the sensor slots. Each of the sensor slots is in fluid communication with a desiccant cavity and is adapted to receive therein one of the blood glucose sensors. The desiccant cavities are relatively shallow cavities for holding desiccant material. The desiccant material is placed in the cavity to insure that the corresponding sensor slot is maintained at an appropriate humidity or desiccate level so that the reagent material in the sensors will not be adversely affect prior to being used.

Prior to loading the sensors into the sensor slots, the front wall of the cylinder is covered with a front burst foil so as to seal the front end of each of the sensor slots. Thereafter, the sensors are loaded into the sensor slots and the desiccant material is disposed in the desiccant cavities. A rear burst foil is then placed over the rear wall so that the sensor slots and desiccant cavities are sealed by the front and rear burst foils.

The sensor instrument has an outer housing with a magazine opening extending laterally through the housing near a front or forward end of the housing. A pivot rod is retracted away from the front end of the instrument allowing the sensor magazine to be placed in the magazine opening. The magazine is positioned in the magazine opening with a detent arm on the instrument housing engaging one of the detent grooves on the magazine to position the magazine in a sensor feeding position. The pivot rod is then moved forward through a central pivot opening in the magazine and an indexing wheel disposed near the rear of the housing. Once locked in an operating position, the pivot rod is keyed to the magazine and the indexing wheel so that the magazine will be rotated as the pivot rod is rotated by the indexing wheel.

After the magazine has been so loaded into the housing, a push rod actuator extending from the top of the instrument housing is pushed forward resulting in a sensor push rod piercing or breaking the rear burst foil and entering a sensor slot. The push rod continues to be moved forward by the push rod actuator until reaching a first detent or sensing position. As the push rod moves forward in the sensor slot, the push rod engages the contact end of the sensor and pushes the sensor out through the front burst foil and into a testing position. When in its testing position, contacts on the sensor mate with contacts in the instrument housing so that the sensor can be coupled through the instrument housing to sensor monitoring equipment. While in this position, the sensor end of the sensor can be placed in a blood sample that needs to be analyzed. Once the test is completed, the push rod is advanced forward further to thereby eject the used sensor from the sensor handling instrument.

As the push rod actuator is moved forward to its testing position and then its ejecting position, a pin extending from the rear of the push rod actuator travels forward in one of a plurality of straight grooves formed in the periphery of the indexing wheel. After the sensor is ejected, the push rod actuator and thereby the push rod are retracted toward the rear of the housing to a standby position. As the push rod actuator is so retracted, the pin extending from the push rod actuator moves within one of a plurality of angled grooves also formed in the periphery of the indexing wheel causing the indexing wheel to rotate until the pin becomes lodged in an adjoining straight groove in the indexing wheel. The rotation of the indexing wheel also results in the pivot rod being rotated because it is keyed to the indexing wheel. The sensor magazine correspondingly is rotated until the detent arm engages another detent groove and another sensor slot is in alignment with the push rod. The sensor handling instrument then is in a condition for supplying another sensor to be used in a blood glucose test.

BRIEF DESCRIPTION OF THE DRAWING

The present invention, together with the above and other objects and advantages, can best be understood from the following detailed description of the embodiment of the invention illustrated in the drawing, wherein:

FIG. 1 is a perspective view of a blood glucose sensor handling instrument embodying the present invention shown with a sensor magazine ready for installation in the instrument;

FIG. 2 is a perspective view of a blood glucose sensor handling instrument of FIG. 1 shown with a sensor magazine installed in the instrument;

FIG. 3 is a rear plan view of the sensor magazine of FIG. 1 with the rear burst foil removed;

FIG. 4 is a front plan view of the sensor magazine of FIG. 1 with the front burst foil removed;

FIG. 5 is an exploded perspective view of the sensor magazine with the front and rear burst foils separated respectively from the front and rear walls of the sensor magazine;

FIG. 6 is side diagrammatic view of the sensor magazine showing how a pivot rod, push rod and a sensor are positioned relative to each other and the sensor magazine;

FIGS. 7–12 are diagrammatic views of the sensor handling instrument of FIG. 1 with a portion of the side of the instrument housing removed so that the operational sequence of use of the sensor handling instrument can be more readily depicted;

DETAILED DESCRIPTION OF THE PREFERRED EMBODIMENT

Figure 13:
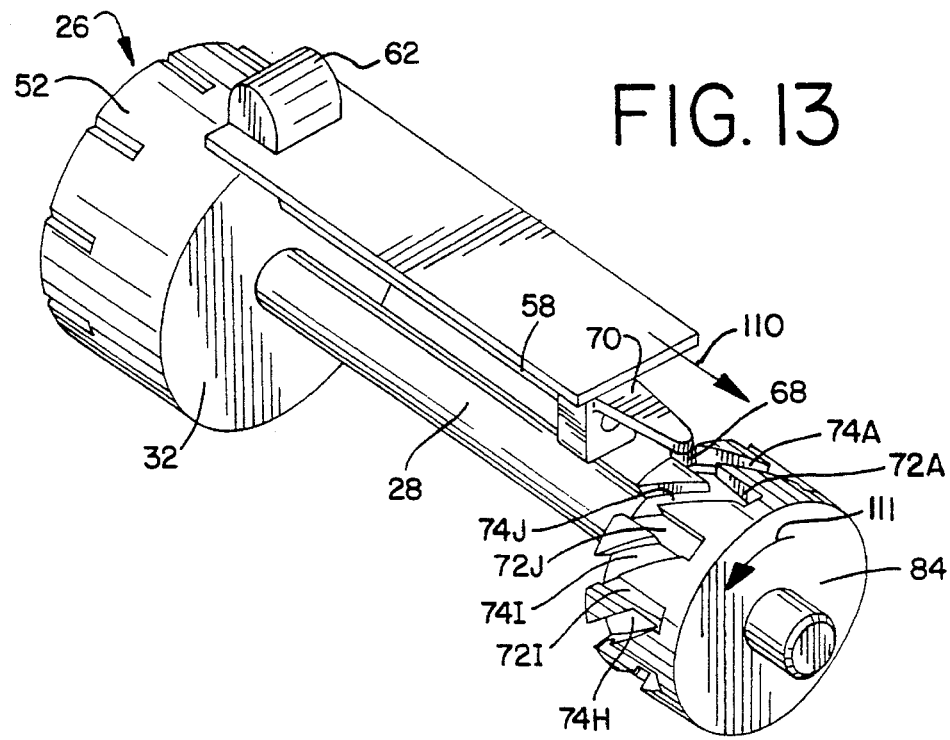
FIG. 13 is a top perspective view of the sensor magazine, the push rod actuator and push rod and the indexing wheel of the sensor handling instrument of FIG. 1 illustrating the relative positions of those components as the push rod actuator is being returned to its standby position.
Figure 15:
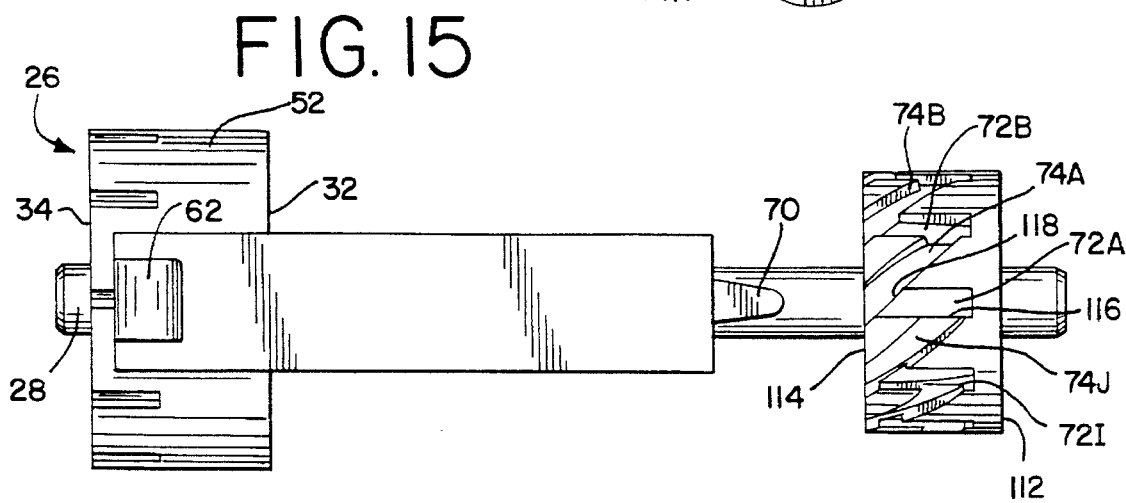
FIG. 15 is a top view of the sensor magazine, the push rod actuator and push rod and the indexing wheel of the sensor handling instrument of FIG. 1 illustrating the relative positions of those components when the push rod actuator is in its forward ejecting position.
Figure 14:
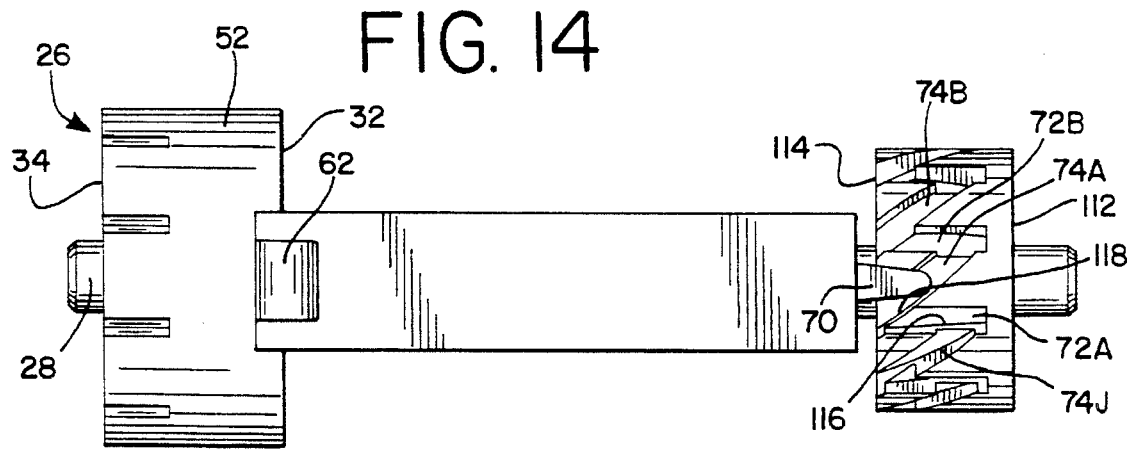
FIG. 14 is a top view of the sensor magazine, the push rod actuator and push rod and the indexing wheel of the sensor handling instrument of FIG. 1 illustrating the relative positions of those components as the push rod actuator is being returned to its standby position.

Referring now more specifically to FIGS. 1–2 of the drawings, therein is disclosed a blood glucose sensor handling or dispensing instrument generally designated by the reference numeral 20 and embodying the present invention. The sensor dispensing instrument 20 has an outer housing 22 with a magazine opening 24 extending laterally therethrough. The magazine opening 24 is adapted to receive a sensor magazine 26 so that it can be rotated by a pivot rod 28 that is extended through the sensor magazine 26. A series of ten sensor slots 30A-J (FIGS. 3–4) extend through the sensor magazine 26 from a rear wall 32 to a front wall 34. Desiccant cavities 36A-J (FIG. 3) respectively are associated with and in fluid communication with the sensor slots 30A-J. Sensors, such as the sensor 38 depicted in FIG. 6, are adapted to be disposed in each of the sensor slots 30A-J. The sensor slots 30A-J with the sensors 38 loaded therein are sealed by a front burst foil 40 that covers the front wall 34 of the sensor magazine 26 and a rear burst foil 42 that covers the rear wall 32 of the sensor magazine 26.

In order to load the sensor magazine 26 into the sensor instrument housing 22, the pivot rod 28 is retracted away from a rear wall 44 of the housing 22 and the sensor magazine 26 is positioned in the magazine opening 24 such that a detent arm 48 extending into the magazine opening 24 engages one of the detent grooves 50A-J on an outer periphery 52 of the magazine 26 (for example, the detent groove 50F depicted in FIG. 4). The pivot rod 28 then is moved forward through a central opening 54 in the sensor magazine 26 and through a indexing wheel 56 located in the housing 22 adjacent the rear wall 44 (see FIGS. 7–15).

With the sensor magazine 26 so disposed in the magazine opening 24, a sensor push or feed rod 58 disposed in the instrument housing 22 near a top wall 60 of the instrument housing 22 is in alignment with one of the sensor slots 30A-J (for example, the sensor slot 30A). When a push rod actuator 62 projecting through a slot 64 in the top wall 60 of the instrument housing 22 is pushed toward a front wall 66 of the instrument housing 22, the sensor push rod 58 pierces the rear burst foil 42 and enters the sensor slot 30A. As the sensor push rod 58 continues to be moved toward the front wall 66 of the housing 22, the sensor push rod 58 engages the sensor 38 disposed in the sensor slot 30A forcing the sensor 38 through the front burst foil 40 into a testing position. While in this testing position, the sensor 38 can be used in connection with analyzing a blood sample. The push rod 58 then can be moved further toward the front wall 66 of the housing 22 by moving the push rod actuator 62 to its forward ejecting position at which time the sensor 38 is ejected from the instrument 20.

As the push rod actuator 62 is moved forward to its testing and ejecting positions, a pin 68 extending from a rear portion 70 of the push rod actuator 62 travels forward in one of a plurality of straight grooves 72A-J extend in the outer periphery of indexing wheel 56 along the longitudinal axis of the indexing wheel 56 (the indexing wheel 56 has ten straight grooves (grooves 72A-B and 72H-J are referenced in FIGS. 7–15) and ten corresponding angled grooves 74A-J extend in the outer periphery of indexing wheel 56 at an angle with respect to the longitudinal axis of the indexing wheel 56 (angled grooves 74A-B and 74G-J are referenced in FIGS. 7 . 15). After the sensor 38 is ejected from the instrument, 20, the push rod actuator 62 and thereby the push rod 58 are retracted toward the rear wall 44 of the housing 22 to a standby position. As the push rod actuator 62 is so retracted, the pin 68 extending from the rear portion 70 of the push rod actuator 62 moves within the angled groove 74A in the indexing wheel 56 causing the indexing wheel 56 to rotate. The pivot rod 28 is keyed to the indexing wheel 56 so that both the pivot rod 28 and the sensor magazine 26 correspondingly are rotated until the detent arm 48 engages another one of the detent grooves 50A-J and another one of the sensor slots 30A-J is in alignment with the push rod 58. The sensor handling instrument 20 then is in a condition for supplying another sensor 38 to be used in a blood glucose test.

As is illustrated in FIGS. 3–5, the sensor magazine 26 has a generally right cylindrical shape and can be made of general purpose polypropylene material. One such type of suitable material is Exxon PD3345. The outer periphery 52 of the sensor magazine 26 includes the ten detent grooves 50A-J. Each of the grooves 50A-J extends a short distance from the front wall 34 of the sensor magazine 26 toward the rear wall 32. As is particularly shown in FIG. 4, each of the detent grooves 50A-J is disposed on the outer periphery 52 of the sensor magazine 26 diametrically opposite to a corresponding one of the sensor slots 30A-J. For example, the sensor slot 30A that is diametrically opposite the detent groove 50F will be in alignment with the push rod 58 when the sensor magazine 26 is rotated such that the detent arm 48 becomes lodged in the detent groove 50F.

Each of the sensor slots 30A-J extends completely through the sensor magazine 26 from the rear wall 32 to the front wall 34 and are generally rectangular in shape so that each of them is adapted to have the sensor 38 disposed therein. The desiccant cavities 36A-J are respectively in fluid communication with the sensor slots 30A-J. The desiccant cavities 36A-J are of relatively shallow depth in that they extend only a short distance into the sensor magazine 26 from the rear wall 32 toward the front wall 34. The actual depth of the desiccant cavities 36A-J is determined by the space that is needed to accommodate a required amount of desiccant material that is to be disposed in each of the desiccant cavities 36A-J. The desiccant material that is disposed in the desiccant cavities 36A-J insures that the sensor slots 30A-J are maintained at an appropriate humidity level so that the reagent material in the sensor 38 disposed in the particular sensor slot 30A-J is not adversely affected prior to being used. The desiccant material might be in the form of a small bag or round bead of material or any other form that can be readily disposed in the desiccant cavities 36A-J. The amount of such desiccant material in the desiccant cavities 36A-J will be dependent on the amount that is required to maintain the sensor slots 30A-J in a desiccate state. One type of desiccant material that could be used is sold under the trademark NATRASORB and is available in powder, pellet and bead forms.

Each of the sensors 38 stored in the sensor magazine 26 is generally flat, rectangular in shape extending from a front or testing end 76 to a rear or contact end 78 (see FIG. 6). The front end 76 has oppositely extending chamfered edges 80 and 82 so that the front end 76 is adapted to puncture the front burst foil 40 when forced out of the sensor slots 30A-J by the push rod 58 and is adapted to be placed into the blood being analyzed. The contact end 78 has contacts (not shown) that are adapted to mate with contacts (not shown) in the instrument housing 22 when the sensor 38 is pushed into its testing position. In this manner, the sensor 38 can be coupled to monitoring equipment (not shown) and the instrument 20 acts as an interface between such monitoring equipment and the sensors 38.

Each of the sensors 38 is provided with a capillary channel that extends from the front, testing end 76 of the sensor 38 to biosensing or reagent material disposed in the sensor 38. When the testing end 76 of the sensor 38 is placed into fluid, such as blood that is accumulated on a person's finger after the finger has been pricked, the fluid is absorbed into the capillary channel by capillary action so that the sensor 38 acts as a wick for the fluid being tested. The fluid then chemically reacts with the reagent material in the sensor 38 so that an electrical signal indicative of the blood glucose level in the blood being tested is supplied to the contacts at the contact end 78 of the sensor 38 and thereby through the instrument 20 to monitoring equipment.

Prior to loading the sensors 38 into the sensor slots 30A-J, the front wall 34 of the sensor magazine 26 is covered with the front burst foil 40. The front burst foil 40 may be made of any material that will adequately seal the sensor slots 30A-J while providing a material that will burst or be pierced when the sensor 38 is pushed forward through the front wall 34 of the sensor magazine 26 by the push rod 58. One type of burst foil that can be used for both the front burst foil 40 and the rear burst foil 42 is AL-191-01 foil distributed by Alusuisse Flexible Packaging, Inc.

With the burst foil 40 in sealing relationship over the front wall 34 of the sensor magazine 26, the sensors 38 are loaded into the sensor slots 30A-J through the rear wall 32 of the sensor magazine 26. In addition, desiccant material is disposed in the desiccant cavities 36A-J. The rear burst foil 42 is secured over the rear wall 32 of the sensor magazine 26 such that the sensor slots 30A-J are sealed between the front burst foil 40 and the rear burst foil 42.

Once the front wall 34 and the rear wall 32 of the sensor magazine 26 are sealed, the sensor magazine 26 may be loaded into the housing 22. The procedure for loading the sensor magazine 26 into the housing 22 and the manner in which the sensor dispensing instrument 20 can be used are generally depicted in FIGS. 7–12. In particular, those figures disclose how the sensor magazine 26 is loaded into the sensor dispensing housing 22, how the sensors 38 contained in the sensor magazine 26 are placed into a testing position and thereafter ejected from the instrument 20, and finally, how the sensor magazine 26 is removed from the sensor dispensing housing 22 so that another sensor magazine 26 can be loaded into the magazine opening 24. In the diagrammatic drawings of FIGS. 7–12, a portion of the outer housing 22 has been removed in order to illustrate the operational sequence of use of the sensor dispensing instrument 20.

In order to load the sensor magazine 26 into the magazine opening 24, the pivot rod 28 has to be retracted so that it does not extend across or into the magazine opening 24. As is illustrated in FIG. 7, a circular or round knob 84 is attached to the rear end of the pivot rod 28. The knob 84 can be pulled away from the rear wall 44 so that the pivot rod 28 is retracted away from the magazine opening 24. As the pivot rod 28 is so retracted, a key 86 extending into a central opening 88 in the indexing wheel 56 will slide within a groove 90 in the periphery of the pivot rod 28. When the pivot rod 28 has been fully retracted from the magazine opening 24, the sensor magazine 26 may be inserted into the magazine opening 24 as indicated by an arrow 92 in FIG. 7. The size of the distal portion 94 of the magazine opening 24 is slightly smaller than the portion of the magazine opening 24 through which the sensor magazine 26 is inserted so that the sensor magazine 26 cannot be accidentally pushed through the distal portion 94 of the magazine opening 24 as it is being loaded into the housing 22. The sensor magazine 26 is disposed in the magazine opening 24 such that the detent arm 48 is lodged in one of the detent grooves 50A-J. For example, the detent arm 48 may be lodged in the detent groove 50F as is illustrated in FIG. 8 so that the sensor magazine 26 is in what can be termed a sensor feeding position.

Once the sensor magazine 26 is so disposed in the magazine opening 24, the knob 84 on the pivot rod 28 can be pushed toward the front wall 66 of the housing 22. As the pivot rod 28 is being moved toward the front wall 66, the pivot rod 28 moves through the central opening 54 in the sensor magazine 26 and into a recess 96 at a forward edge 98 of the magazine opening 24. The pivot rod 28 also will slide through the central opening 88 in the indexing wheel 56 but remained keyed to the indexing wheel 56 due to the fact that the key 86 extending from the indexing wheel 56 remains lodged in the groove 90 in the periphery of the pivot rod 28.

The pivot rod 28 is configured (FIG. 6) so that it is adapted to lodge in the central opening 54 of the sensor magazine 26 such that the sensor magazine 26 will be rotated as the pivot rod 28 is rotated. For example, the pivot rod 28 can be keyed to the central opening 54 in the sensor magazine 26 like it is keyed to the indexing wheel 56.

The engagement of the detent arm 48 into the detent groove 50F insures that a corresponding sensor slot 30A is in alignment with the push rod 58. When a user of the sensor handling instrument 20 needs to use one of the sensors 38 to analyze a blood sample, the push rod actuator 62 that extends through the slot 64 in the top wall 60 of the housing 22 is pushed toward the front wall 66 of the housing 22 as indicated by an arrow 100 in FIG. 9. The push rod actuator 62 is connected to the push rod 58 such that the push rod 58 also is moved toward the front wall 66 of the housing 22. A forward end 102 of the push rod 58 is somewhat pointed so that as it is moved forward, it pierces the rear burst foil 42, enters into the sensor slot 30A, and engages the contact end 78 of the sensor 38 disposed in the sensor slot 30A,, The continued movement of the push rod actuator 62 and thereby the push rod 58 in the direction of the arrow 100 results in the sensor 38 in the sensor slot 30A being thrust forward in the sensor slot 30A resulting in the front, chamfered end 76 of the sensor 38 piercing through the front burst foil 40.

The push rod actuator 62 is moved in the direction of the arrow 100 until it reaches a testing detent position as is illustrated in FIG. 9 of the drawings. When the push rod 58 has been advanced to this testing position, the sensor 38 is disposed in a groove 104 that extends from the front wall 66 to the forward edge 98 of the magazine opening 24. As is illustrated in FIG. 9, the sensor 38 extends out from the front wall 66 of the housing 22 when it is in this testing position so that the testing end 76 of the sensor 38 can be placed in the fluid being tested. Moreover, contacts near the contact end 78 of the sensor 38 engage or become mated with contacts in the groove 104 so that the electrical signals developed in the sensor 38 due to the absorption of fluid being tested can be transmitted to monitoring equipment.

As the push rod actuator 62 is moved forward to its testing position, the pin 68 extending from the rear portion 70 of the push rod actuator 62 travels forward in the straight groove 72A disposed in the indexing wheel 56 (see FIGS. 7–9). The straight groove 72A is in alignment with the sensor slot 30A so that the movement of the pin 68 within the straight groove 72A does not rotate or otherwise move the indexing wheel 56. Consequently, the pivot rod 28 and thereby the sensor magazine 26 likewise are not rotated as the push rod actuator 62 is moved forward to its testing position.

Once the testing of the blood or other fluid is completed, the used sensor 38 that was in the sensor slot 30A needs to be ejected from the instrument 20. This is readily accomplished by moving the push rod actuator 62 further forward toward the front wall 66 in the direction of an arrow 106 in FIG. 10. As the push rod actuator 62 is moved in the direction of the arrow 106, the push rod 58 forces the used sensor 38 out of the groove 104 as is depicted in FIG. 10. The push rod actuator 62 is advanced until it is in the ejection position shown in FIG. 10 at which time the used sensor 38 becomes dislodged from the instrument 20.

In order to have the instrument 20 again be placed into a standby or ready condition so that another sensor 38 can be placed into a testing position, the push rod actuator 62 is returned to its standby condition by moving it in the direction of an arrow 108 in FIG. 11. As the push rod actuator 62 is being returned to its standby position, the push rod 58 correspondingly is retracted out of the sensor slot 30A. In addition, the pin 68 on the rear portion 70 of the push rod actuator 62 will enter into the angled groove 74A in the indexing wheel 56 as the push rod 58 is cleared from the rear wall 32 of the sensor magazine 26. As the pusher rod actuator 62 is moved in the direction of an arrow 110 in FIG. 13, the pin 68 travels along the angled groove 74A and the indexing wheel 56 will be forced to rotate in the direction of an arrow 111 in FIG. 13. The continued retraction of the push rod actuator 62 towards the rear wall 44 of the housing 22 results in the pin 68 traveling in the angled groove 74A until it becomes lodged in the adjacent straight groove 72B. It is noted that the straight grooves 72A-J are inclined somewhat as they extend from a rear end 112 of the indexing wheel 56 toward a forward end 114 of the indexing wheel 56 (see in particularly FIGS. 13–15). As a result, a step is formed between adjacent angled grooves 74A-J and straight grooves 72A-J to insure that the pin 68 will travel only in the straight grooves 72A-J as the push rod actuator 62 moves forward toward the front wall 66 of the housing 22 and only in the angled grooves 74A-J as the push rod actuator 62 is retracted toward the rear wall 44 of the housing 22. For example, a step 116 is formed between the angled groove 74J and the adjacent straight groove 72A near the rear end 112 of the indexing wheel 56 (see FIG. 15). This step 116 is a down step from the higher rear portion of the angled groove 74J to the lower rear portion of the straight groove 72A. The step 116 blocks or prevents the pin 68 from reentering the angled groove 74J as the push rod actuator 62 is advanced forward to its testing position. Similarly, a step 118 is formed between the straight groove 72A and the adjacent angled groove 74A near the front end, 114 of the indexing wheel 56 (see FIG. 15). This step 118 is a down step from the higher front portion of the straight groove 72A to the lower front portion of the angled groove 74A. Consequently, the step 118 blocks or prevents the pin 68 from reentering the straight groove 72A as the push rod actuator 62 is retracted, to its standby position.

The rotation of the indexing wheel 56 caused by the movement of the pin 68 in the angled groove 74A results in the sensor magazine 26 being rotated in the direction of the arrow 111 in FIG. 13 for a total of 36 degrees until the detent arm 48 becomes lodged in the next detent groove 50E on the periphery 52 of the sensor magazine 26 such that the next sensor slot 30J is in alignment with the push rod 58. The sensor 38 disposed in the sensor slot 30J can be dislodged from the sensor slot 30J for use in testing blood or the like in the same manner as the sensor 38 in the sensor slot 30A was placed in its testing position.

The above sequence of placing the sensor 38 disposed in the sensor slot 30A into a testing position and thereafter ejecting it from the instrument 20 can be repeated for each of the sensors disposed in the remaining sensor slots 30B-I until all of the sensors 38 in the sensor magazine 26 are used. Thereafter, the knob 84 can be retracted in the direction of an arrow 120 in FIG. 12 so that the sensor magazine 26 can be removed from the magazine opening 24 as indicated by another arrow 122 in FIG. 12 and a new sensor magazine 26 can be inserted into the magazine opening 24 as is illustrated in FIG. 7.

The sizes for the components of the sensor instrument 20 can vary depending on the particular use for which the instrument 20 is designed. In one configuration of the instrument 20, the outer diameter of the sensor magazine 26 is 1.210 inches (30.75 mm) and the depth of the sensor magazine 26 from the rear wall 32 to the front wall 34 is 0.670 inches (17.02 mm). When such a dimensional sensor magazine 26 is used, the sensors 38 can have a length dimension from the front end 76 to the contact end 78 of 0.650 inches (16.51 mm), a width of 0.200 inches (5.08 mm), and a front dimension of 0.40 inches (10.16 mm) between the chamfered edges 80 and 82; the pivot rod 28 can have an outer thickness dimension of 0.125 (3.17 mm); and the push rod 58 can have an outer thickness dimension of 0.62 inches (1.57 mm). In such a specifically configured instrument 20, the push rod 58 may be positioned approximately 0.057 inches (1.46 mm) away from the rear wall 32 of the sensor magazine 26 when the instrument 20 is in its standby condition. The stroke of the push rod 58 to feed the sensor 38 from within one of the sensor slots 30A-J to its testing position would be approximately 0.752 inches (19.10 mm). In order to eject the sensor 38 from the housing 22, the further stroke of the push rod 58 would be approximately 0.282 inches (7.17 mm). When the sensor magazine 26 is to be loaded into or removed from the magazine opening 24, the pivot rod 28 is moved a stroke of approximately 0.797 inches (20.25 mm).

While the invention has been described with reference to details of the illustrated embodiment, these details are not intended to limit the scope of the invention as defined in the appended claims. For example, the instrument 20 can be used for testing fluids other than blood glucose. In fact, the instrument 20 can be used in connection with analyzing any type chemistry fluid that can be analyzed by means of a reagent material.

What is claimed and desired to be secured by Letters Patent of the United States is:

1. A sensor dispensing instrument for handling of a plurality of fluid sensors comprising:

a housing having a magazine opening;

a sensor magazine adapted to be disposed in said magazine opening, said sensor magazine having a plurality of sensor slots each of which sensor slots is adapted to accommodate one of said plurality of fluid sensors;

a feed means;

a pivot means engageable with said sensor magazine when said sensor magazine is disposed in said magazine opening for turning said sensor magazine so that one of said plurality of sensor slots is in alignment with said feed means;

indexing means associated with said pivot means to turn said pivot means as said indexing means turns; and feed actuator means connected to said feed means for advancing said feed means through said sensor slot in alignment with said feed means so that said sensor in said sensor slot is placed into a testing position, wherein a portion of one end of said sensor protrudes from said instrument for further advancing said feed means so that said sensor is ejected from said instrument, and for returning said feed means to a standby position, said feed actuator means being operatively associated with said indexing means to turn said indexing means as said feed actuator means returns said feed means to said standby position to thereby turn said sensor magazine so that another of said plurality of sensor slots is in alignment with said feed means.

2. A sensor dispensing instrument as set forth in claim 1 wherein said sensor magazine is a right cylinder having a plurality of detent means along its outer periphery, each of said detent means corresponding to one of said plurality of sensor slots.

3. A sensor dispensing instrument as set forth in claim 2 wherein said detent means and said sensor slots are equally spaced on said sensor magazine.

4. A sensor dispensing instrument as set forth in claim 2 including a detent arm means projecting into said magazine opening, one of said plurality of sensor slots being in alignment with said feed means when said detent arm means is disposed in one of said plurality of detent means.

5. A sensor dispensing instrument as set forth in claim 1 wherein said sensor magazine includes a plurality of desiccant cavities, each of which desiccant cavities is in fluid communication with one of said plurality of sensor slots.

6. A sensor dispensing instrument as set forth in claim 5 including desiccant material in each of said plurality of desiccant cavities so that each of said plurality of sensor slots is maintained in a desiccate state.

7. A sensor dispensing instrument as set forth in claim 5 wherein said sensor magazine includes first and second walls with each of said plurality of desiccant cavities extending from said first wall toward said second wall and including first foil means covering said first wall such that said plurality of desiccant cavities are sealed by said first foil means.

8. A sensor dispensing instrument as set forth in claim 1 wherein said sensor magazine includes first and second walls with each of said plurality of sensor slots extending from said first wall to said second wall and including first foil means covering said first wall and a second foil means covering said second wall such that said plurality of sensor slots are sealed between said first and second foil means.

9. A sensor dispensing instrument as set forth in claim 8 wherein as said feed means is being advanced by said feed actuator means said feed means pierces said first foil means, enters into said sensor slot in alignment with said feed means and engages said sensor in said sensor slot forcing said sensor to pierce through said second foil means into said testing position.

10. A sensor dispensing instrument as set forth in claim 9 wherein each of said plurality of sensors includes a chamfered testing end that is adapted to pierce said second foil means and that is adapted to be placed in fluid to be tested.

11. A sensor dispensing instrument as set forth in claim 1 wherein said pivot means has a first position in engagement with said sensor magazine so that as said pivot means is rotated said sensor magazine is rotated and a second position retracted away from said magazine opening so that said sensor magazine can be inserted into or removed from said magazine opening.

12. A sensor dispensing instrument as set forth in claim 1 wherein said indexing means has a plurality of first grooves extending along a longitudinal axis of said indexing means and a plurality of second grooves disposed at an angle with respect to said first grooves and said feed actuator means has a pin that travels in one of said first grooves as said feed means is moved toward said sensor slot and travels in one of said second grooves as said feed means is returned to its standby position such that said indexing means is rotated as said pin travels in one of said second grooves.

13. A sensor dispensing instrument as set forth in claim 12 wherein each of said second grooves extend in an outer periphery of said indexing means from one of said plurality of first grooves to the next adjacent one of said plurality of first grooves,

14. A sensor dispensing instrument as set forth in claim 13 including first step means between adjacent first and second grooves preventing said pin from traveling in said second grooves when said feed actuator means is advanced towards said sensor magazine and second step means between adjacent first and second grooves preventing said pin from traveling in said first grooves when said feed actuator means is being returned to said standby position.

15. A method of handling a plurality of fluid sensors comprising:

installing a sensor magazine into a magazine opening in a housing of a sensor dispensing instrument, said sensor magazine having a plurality of sensor slots, each of which sensor slots is adapted to accommodate one of said plurality of fluid sensors;

positioning said sensor magazine so that one of said plurality of sensor slots is in alignment with a feed means;

actuating a feed actuator means to advance said feed means through said sensor slot in alignment with said feed means so that said sensor in said sensor slot is placed into a testing position wherein a portion of one end of said sensor protrudes from said instrument;

further actuating said feed actuator means so that said feed means is further advanced to eject said sensor from said instrument;

returning said feed actuator means to a standby position so as to return said feed means to a standby position with said feed actuator means causing an indexing wheel in said housing to be rotated as said feed means is returned to said standby position to thereby rotate said sensor magazine so that another one of said plurality of sensor slots is placed in alignment with said feed means.

16. A method of handling a plurality of fluid sensors as set forth in claim 15 wherein said sensor magazine includes first and second walls with each of said plurality of sensor slots extending from said first wall to said second wall and including first foil means covering said first wall and a second foil means covering said second wall such that said plurality of sensor slots are sealed between said first and second foil means and wherein said feed means pierces said first foil as said feed means is advanced into said sensor slot and said sensor pierces said second foil as said feed means advances said sensor into said testing position.

17. A method of handling a plurality of fluid sensors as set forth in claim 15 wherein said indexing wheel has a plurality of first grooves extending along a longitudinal axis of said indexing wheel and a plurality of second grooves disposed at an angle with respect to said first grooves and said feed actuator means has a pin that travels in one of said first grooves as said feed means is moved toward said sensor slot and travels in one of said second grooves as said feed means is returned to its standby position such that said indexing wheel is rotated as said pin travels in one of said second grooves.

18. A method of handling a plurality of fluid sensors as set forth in claim 17 wherein each of said second grooves extends in an outer periphery of said indexing wheel from one of said plurality of first grooves to the next adjacent one of said plurality of first grooves.

\* \* \* \* \*